(12) United States Patent
Ito et al.

(10) Patent No.: US 9,056,805 B2
(45) Date of Patent: Jun. 16, 2015

(54) BUTANOL MANUFACTURING METHOD

(75) Inventors: Masateru Ito, Kamakura (JP); Izumi Morita, Kamakura (JP); Shinichi Yamane, Tokyo (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 296 days.

(21) Appl. No.: 13/635,066

(22) PCT Filed: Mar. 16, 2011

(86) PCT No.: PCT/JP2011/056161
§ 371 (c)(1),
(2), (4) Date: Oct. 31, 2012

(87) PCT Pub. No.: WO2011/115151
PCT Pub. Date: Sep. 22, 2011

(65) Prior Publication Data
US 2013/0041187 A1   Feb. 14, 2013

(30) Foreign Application Priority Data
Mar. 17, 2010   (JP) .................. 2010-060946

(51) Int. Cl.
*C07C 29/74* (2006.01)
*C07B 63/00* (2006.01)
*B01D 61/02* (2006.01)
*C07C 29/76* (2006.01)

(52) U.S. Cl.
CPC .............. *C07B 63/00* (2013.01); *B01D 61/022* (2013.01); *B01D 61/025* (2013.01); *B01D 61/027* (2013.01); *B01D 2311/06* (2013.01); *B01D 2311/2646* (2013.01); *C07C 29/76* (2013.01)

(58) Field of Classification Search
CPC ...................................................... C07C 29/74
USPC .......................................................... 568/913
See application file for complete search history.

(56) References Cited

U.S. PATENT DOCUMENTS

2009/0171129 A1 * 7/2009 Evanko et al. ................ 568/916
2009/0305374 A1   12/2009 Retsina et al.
2011/0004018 A1   1/2011 Ito et al.

FOREIGN PATENT DOCUMENTS

| CA | 2718258 A1 * | 9/2009 |
| JP | 2006/151821 A | 6/2006 |
| JP | 2010-143888 A | 7/2010 |
| WO | WO 2007/146377 A1 | 12/2007 |
| WO | WO 2009/086391 A2 | 7/2009 |
| WO | WO 2009/113565 A1 | 9/2009 |

* cited by examiner

*Primary Examiner* — Porfirio Nazario Gonzalez
*Assistant Examiner* — Kofi Adzamli
(74) *Attorney, Agent, or Firm* — Birch, Stewart, Kolasch & Birch, LLP (57) ABSTRACT

Highly pure butanol can be produced by a method for producing butanol, the method comprising: Step A, wherein a butanol-containing solution is filtered through a nanofiltration membrane and a butanol-containing solution is recovered from the permeate side; Step B, wherein the butanol-containing solution obtained in Step A is passed through a reverse osmosis membrane and thereby concentrated to cause two-phase separation into a butanol phase and an aqueous phase; and Step C, wherein butanol is recovered from the butanol phase obtained in Step B.

16 Claims, 2 Drawing Sheets

BUTANOL MANUFACTURING METHOD

TECHNICAL FIELD

The present invention relates to a method for producing butanol by separating butanol from a butanol-containing solution.

BACKGROUND ART

Butanol is a compound which is industrially very important as a raw material of chemicals and pharmaceuticals, and as a solvent and a fuel. Butanol is generally produced by a chemical synthesis method using propylene as a raw material (oxo method), but, in view of the recent problems of decrease in the crude oil resource and sharp rise in its prices, and GHG (greenhouse gas) emission control, technologies for butanol production by microbial fermentation using biomass, which is non-fossil material, as raw material have been drawing attention, and several such technologies have been reported (e.g., Patent Document 1). However, in general, production of butanol by microbial fermentation allows accumulation of butanol in the fermentation broth up to only about 1 to 3% by weight, because of inhibition of the growth of the microorganism by butanol. Therefore, in order to obtain pure butanol from the fermentation broth, a large quantity of water contained in the fermentation broth needs to be removed. As a common method for removal of water, vacuum heating is employed, but removal of water is difficult because butanol has a property to easily undergo azeotropy with water.

In Patent Document 2, as a method for separating/purifying butanol from a butanol-containing solution produced by microbial fermentation, a method is disclosed wherein a fermentation broth is concentrated with a reverse osmosis membrane and the butanol phase of the resulting two-phase-separated concentrate is subjected to distillation to recover butanol. However, fermentation broths generally contain impurities such as inorganic salts, saccharides and proteins derived from fermentation media; and alcohols and organic acids generated as side products. These impurities easily cause fouling of the membrane and the osmotic pressure may be increased thereby, resulting in requirement of a higher pressure to achieve concentration of the broth to a level at which two-phase separation occurs. Further, in cases where an impurity having surface activity is contained, two-phase separation is less likely to occur, which is problematic. Still further, since impurities such as colored components are contained in the butanol phase, it may be difficult to purify, by distillation, butanol at high purity with low degree of coloration, which is problematic. Since Patent Document 2 describes neither examples using a reverse osmosis membrane nor effects of impurities in cases of concentration through a reverse osmosis membrane, it has not been clear whether the method described in Patent Document 2 can be applied to production of butanol.

Further, Patent Document 3 discloses a method for recovering a solvent contained in a dilute aqueous solution with a nanofiltration membrane, and butanol is included as a specific example of the solvent. This method aims to recover a solvent such as butanol from the feed side of the nanofiltration membrane, and the mechanism of recovery of butanol in this method suggests to those skilled in the art that a nanofiltration membrane is not permeable to butanol. Patent Document 3 does not disclose any actual example of filtration of a butanol-containing solution through a nanofiltration membrane, and there is no description on the two-phase separability of the recovered aqueous butanol solution.

PRIOR ART DOCUMENTS

Patent Documents

[Patent Document 1] Japanese Translated PCT Patent Application Laid-open No. 2009-539407
[Patent Document 2] WO2009/086391
[Patent Document 3] JP 2006-151821 A

SUMMARY OF THE INVENTION

Problems to be Solved by the Invention

The present invention aims to provide, in order to solve the above problems, a method for separating highly pure butanol from a butanol-containing solution.

Means for Solving the Problems

The present inventors intensively studied to solve the above problems, and, in this process, unexpectedly discovered that nanofiltration membranes are permeable to butanol. Based on this fact, the present inventors discovered that highly pure butanol can be recovered at high efficiency with less input energy by filtering a butanol-containing solution through a nanofiltration membrane and recovering a butanol-containing solution from the permeate side, followed by passing the obtained butanol-containing solution through a reverse osmosis membrane to increase the butanol concentration, thereby completing the present invention.

That is, the present invention is constituted by (1) to (11) below.

(1) A method for producing butanol, the method comprising:

Step A, wherein a butanol-containing solution is filtered through a nanofiltration membrane and a butanol-containing solution is recovered from the permeate side;

Step B, wherein the butanol-containing solution obtained in Step A is passed through a reverse osmosis membrane and thereby concentrated to cause two-phase separation into a butanol phase and an aqueous phase; and Step C, wherein butanol is recovered from the butanol phase obtained in Step B.

(2) The method for producing butanol according to (1), wherein the butanol is n-butanol or isobutanol.

(3) The method for producing butanol according to (1) or (2), wherein the butanol-containing solution is a fermentation broth obtained by microbial fermentation.

(4) The method for producing butanol according to any of (1) to (3), wherein a functional layer of the nanofiltration membrane comprises a polyamide.

(5) The method for producing butanol according to any of (1) to (4), wherein the polyamide comprises a cross-linked piperazine as a major component and further comprises a constituting component represented by Chemical Formula 1:

Chemical Formula (1)

(wherein R represents —H or —CH$_3$, and n represents an integer of 0 to 3).

(6) The method for producing butanol according to any of (1) to (5), wherein, in Step B, the temperature of the butanol-containing solution during the concentration is within the range of 4 to 60° C.

(7) The method for producing butanol according to any of (1) to (6), wherein, in Step B, the concentration is carried out such that the butanol concentration in the concentrate is not less than 8% by weight.

(8) The method for producing butanol according to any of (1) to (7), wherein the aqueous phase is recycled into the flow to be passed through the nanofiltration membrane in Step A and/or the reverse osmosis membrane in Step B.

(9) The method for producing butanol according to any of (1) to (8), wherein the recovered butanol phase is purified by distillation in Step C.

(10) The method for producing butanol according to (9), wherein the butanol-containing solution recovered from the vapor side in the purification by distillation is recycled into the flow to be passed through the nanofiltration membrane in Step A and/or the reverse osmosis membrane in Step B.

(11) The method for producing butanol according to (9) or (10), wherein the butanol-containing solution recovered from the liquid side in the purification by distillation is further subjected to purification by distillation, followed by recovering butanol from the vapor side.

Effect of the Invention

By the present invention, highly pure butanol can be separated at high efficiency from a butanol-containing solution.

DESCRIPTION OF SYMBOLS

1. Tank for raw liquid to be filtered through nanofiltration membrane
2. Nanofiltration membrane module
3. Reverse osmosis membrane module
4. Extraction vessel
5. Distillation column
6. Flow of aqueous butanol solution
7. Flow of butanol-containing permeate
8. Non-permeated liquid containing a large amount of impurities
9. Flow of non-permeated liquid containing concentrated butanol
10. Permeate that substantially does not contain butanol and contains water
11. Flow of aqueous phase containing butanol in the amount equivalent to the saturation solubility
12. Aqueous phase
13. Butanol phase
14. Flow of butanol phase
15. Flow of butanol at high purity
16. Flow containing butanol and water
17. High pressure pump
18. Tank for raw liquid to be filtered through reverse osmosis membrane
19. High pressure pump
20. Flow of liquid that did not permeate through reverse osmosis membrane

BEST MODE FOR CARRYING OUT THE INVENTION

The present invention will now be described in more detail.

Butanol in the present invention is a general term for monovalent alcohols having 4 carbon atoms, and specific examples of the butanol include n-butanol (1-butanol), isobutanol, 2-butanol and 2-methyl-2-propanol. The butanol may comprise either a single type or a plurality of types of such butanols, and the present invention is preferably applied to a method for producing n-butanol or isobutanol.

The method for producing the butanol-containing solution used in the present invention is not restricted as long as it is a method known to those skilled in the art. In cases where a chemical synthesis method is used, specific examples of the method include synthesis from acetaldehyde by the Wacker process and synthesis from propylene, carbon monoxide and water by the Reppe process. The butanol-containing solution can also be produced by fermentation culture of a microorganism, such as anaerobic culture of *Clostridium butylicum*.

A preferred method for producing the butanol-containing solution used in the present invention is fermentation culture of a microorganism. That is, the butanol-containing solution used in the present invention is preferably a fermentation broth obtained by fermentation culture of a microorganism. For example, in cases where the butanol is isobutanol, an isobutanol-containing solution can be preferably produced by the method described in US 2009/0226991 B; Appl Microbiol Biotechnol (2010) 85, 651-657; Current Opinion in Biotechnology (2009) 20, 307-315; or the like, and, in cases where the butanol is n-butanol, an n-butanol-containing solution can be preferably produced by the method described in Acetone-butanol Fermentation (p. 19) in Fermentation Handbook (ed. Japan Bioindustry Association) or the like.

The present invention is constituted by: Step A, wherein a butanol-containing solution is filtered through a nanofiltration membrane and a butanol-containing solution is recovered from the permeate side; Step B, wherein the butanol-containing solution obtained in Step A is passed through a reverse osmosis membrane and thereby concentrated to cause two-phase separation into a butanol phase and an aqueous phase; and Step C, wherein butanol is recovered from the butanol phase obtained in Step B. Each Step of the present invention will now be described in more detail.

(Step A)

The nanofiltration membrane used in the present invention is also called a nanofilter (nanofiltration membrane, NF membrane), and generally defined as "membrane that allows permeation of monovalent ions, but blocks divalent ions". The membrane is considered to have fine voids having sizes of about several nanometers, and mainly used to block fine particles, molecules, ions, salts and the like in water.

The term "filtration through a nanofiltration membrane" means that the butanol-containing solution is filtered through a nanofiltration membrane to remove impurities, which are substances other than butanol, mainly into the feed side, while a butanol-containing solution is recovered from the permeate side. For example, in cases where the butanol-containing solution is a fermentation broth produced by fermentation culture of a microorganism, the fermentation broth is filtered through a nanofiltration membrane to remove, block or separate impurities such as inorganic acids, saccharides, organic acids and colored components which are dissolved or precipitated as solids, while a butanol-containing solution is allowed to permeate as a filtrate. Since the non-permeated liquid containing impurities also contains butanol, the non-permeated liquid is preferably recycled into the raw liquid (feed liquid) in order to increase the recovery of butanol.

Examples of known materials of nanofiltration membranes generally include macromolecular materials such as cellulose acetate polymers, polyamides, polyesters, polyimides and vinyl polymers. In the present invention, a nanofiltration membrane having a polyamide in its functional layer is preferably used because of its high purification efficiency. Other plural membrane materials may also be contained in the membrane as long as the functional layer contains a polyamide. In terms of the membrane structure, either an asymmetric membrane wherein at least one side of the membrane has a dense layer, which membrane has micropores having a diameter that gradually increases from the dense layer to the inside of the membrane or to the other side of the membrane, or a composite membrane having on the dense layer of an asymmetric membrane a very thin functional layer formed by another material can be used. Examples of the composite membrane which may be used include the composite membrane described in JP 62-201606 A, wherein a nanofiltration membrane having a polyamide functional layer was placed on a support membrane made of a polysulfone membrane material.

The nanofiltration membrane having a polyamide functional layer preferably used in the present invention is a composite membrane having high pressure resistance, high permeability to water and high solute removal performance. Further, in order to allow maintenance of durability against the operating pressure, high permeability to water and high blocking performance, the membrane preferably has a structure in which a polyamide functional layer is retained by a support made of a porous membrane or non-woven fabric. For a nanofiltration membrane having a polyamide functional layer, preferred examples of the carboxylic component of the monomers constituting the polyamide include aromatic carboxylic acids such as trimesic acid, benzophenone tetracarboxylic acid, trimellitic acid, pyromellitic acid, isophthalic acid, terephthalic acid, naphthalenedicarboxylic acid, diphenylcarboxylic acid and pyridinecarboxylic acid, and, in view of solubility to a film-forming solvent, trimesic acid, isophthalic acid or terephthalic acid, or a mixture thereof is more preferred.

Preferred examples of the amine component of the monomers constituting the polyamide include primary diamines having an aromatic ring(s), such as m-phenylenediamine, p-phenylenediamine, benzidine, methylenebisdianiline, 4,4'-diaminobiphenyl ether, dianisidine, 3,3',4-triaminobiphenyl ether, 3,3',4,4'-tetraminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-aminobenzoyl)-p(m)-phenylenediamine-2,2'-bis(4-aminophenyl benzimidazole), 2,2'-bis(4-aminophenyl benzoxazole) and 2,2'-bis(4-aminophenyl benzothiazole); and secondary diamines such as piperazine and piperidine and derivatives thereof; and, in particular, a nanofiltration membrane having a functional layer composed of a cross-linked polyamide containing piperazine or piperidine as monomers has high pressure resistance and durability as well as heat resistance and chemical resistance, and is therefore preferably used. The polyamide more preferably comprises a cross-linked piperazine polyamide or cross-linked piperidine polyamide as a major component and further comprises a constituting component represented by the Chemical Formula 1. The polyamide still more preferably comprises a cross-linked piperazine polyamide as a major component and further comprises a constituting component represented by the Chemical Formula 1. Further, preferably, in the Chemical Formula 1, n=3. Examples of the nanofiltration membrane having a polyamide functional layer comprising a cross-linked piperazine polyamide as a major component and further comprising a constituting component represented by the Chemical Formula 1 include the one described in JP 62-201606 A, and specific examples of such a nanofiltration membrane include the cross-linked piperazine polyamide nanofiltration membrane UTC60 manufactured by Toray Industries, Inc., which has a polyamide functional layer comprising a cross-linked piperazine polyamide as a major component and further comprising a constituting component represented by the Chemical Formula 1 wherein n=3.

A nanofiltration membrane is generally used as a spiral-wound membrane module, and the nanofiltration membrane used in the present invention is also preferably used as a spiral-wound membrane module. Specific examples of preferred nanofiltration membrane modules include a nanofiltration membrane GE Sepa, manufactured by GE Osmonics, which is a cellulose acetate nanofiltration membrane; nanofiltration membranes NF99 and NF99HF, manufactured by Alfa-Laval, which have polyamide functional layers; nanofiltration membranes MPS-34 and MPS-36, manufactured by KOCH; nanofiltration membranes NF-45, NF-90, NF-200, NF-270 and NF-400, manufactured by FilmTec Corporation, which have cross-linked piperazine polyamide functional layers; and nanofiltration membrane modules SU-210, SU-220, SU-600, SU-610 and SU-620, manufactured by Toray Industries, Inc., comprising UTC60, manufactured by the same manufacturer, which has a polyamide functional layer comprising a cross-linked piperazine polyamide as a major component and further comprising a constituting component represented by the Chemical Formula 1. The nanofiltration membrane module is preferably the nanofiltration membrane NF99 or NF99HF, manufactured by Alfa-Laval, which has a polyamide functional layer; nanofiltration membrane NF-45, NF-90, NF-200 or NF-400, manufactured by FilmTec Corporation, which has a cross-linked piperazine polyamide functional layer; nanofiltration membrane MPS-34 or MPS-36, manufactured by KOCH; or nanofiltration membrane module SU-210, SU-220, SU-600, SU-610 or SU-620, manufactured by Toray Industries, Inc., comprising UTC60, manufactured by the same manufacturer, which has a polyamide functional layer comprising a cross-linked piperazine polyamide as a major component and further comprising a constituting component represented by the Chemical Formula 1. The nanofiltration membrane module is more preferably the nanofiltration membrane module SU-210, SU-220, SU-600, SU-610 or SU-620, manufactured by Toray Industries, Inc., comprising UTC60, manufactured by the same manufacturer, which has a polyamide functional layer comprising a cross-linked piperazine polyamide as a major component and further comprising a constituting component represented by the Chemical Formula 1.

Examples of the method for evaluating the extent of removal, blocking or separation of impurities dissolved or precipitated as solids by the nanofiltration membrane used in the present invention include an evaluation method by calculating an inorganic ion removal rate (blocking rate), but the method is not restricted to this method. The inorganic salt removal rate (blocking rate) can be calculated by measuring the concentration of an inorganic salt contained in the raw liquid (feed liquid) (raw liquid inorganic salt concentration) and the concentration of the inorganic salt contained in the permeate (permeate inorganic salt concentration) by an analysis represented by ion chromatography, and using Equation 1.

Inorganic salt removal rate (%)=(1−(permeate inorganic salt concentration/raw liquid inorganic salt concentration))×100   (Equation 1)

In terms of the membrane separation performance of the nanofiltration membrane used in the present invention, the nanofiltration membrane preferably shows a removal rate, calculated according to Equation 1, of not less than 45% when sodium chloride (500 mg/L) at a temperature of 25° C. and a pH of 6.5 is used.

In terms of the permeation performance of the nanofiltration membrane, a nanofiltration membrane in which the permeation flow rate of sodium chloride (500 mg/L) per unit membrane area ($m^3/m^2$/day) at a filtration pressure of 0.3 MPa is not less than 0.5 is preferably used. The permeation flow rate per unit membrane area (membrane permeation flux) can be calculated by measuring the amount of the permeate, collection time of the permeate and the membrane area, and using Equation 2.

Membrane permeation flux ($m^3/m^2$/day)=amount of permeate/membrane area/collection time   (Equation 2)

The permeability of a nanofiltration membrane to butanol upon separation of butanol from an aqueous butanol solution by the above method can be evaluated by calculating the butanol permeation rate. The butanol permeation rate can be calculated by measuring the concentration of butanol contained in the raw liquid (feed liquid) (raw liquid butanol concentration) and the concentration of butanol contained in the permeate (butanol-containing solution) (permeate butanol concentration) by an analysis represented by high performance liquid chromatography, and using Equation 3.

Butanol membrane permeation rate (%)=(permeate butanol concentration/raw liquid butanol concentration)×100   (Equation 3)

The filtration through a nanofiltration membrane may be carried out under pressure, and the filtration pressure is preferably within the range of 0.1 MPa to 8 MPa. In cases where the filtration pressure is less than 0.1 MPa, the membrane permeation rate may decrease, while in cases where the filtration pressure is more than 8 MPa, the membrane may be damaged. In cases where the membrane is used at a filtration pressure within the range of 0.5 MPa to 7 MPa, the membrane permeation flux is high, so that the aqueous butanol solution can be efficiently allowed to permeate and the possibility of damaging the membrane is small, which is more preferred. The membrane is especially preferably used at a filtration pressure within the range of 1 MPa to 6 MPa.

(Step B)

The term "passed through a reverse osmosis membrane and thereby concentrated" in the present invention means that the butanol-containing solution obtained in Step A is passed through a reverse osmosis membrane and a concentrate containing butanol is recovered into the feed side, while water is mainly allowed to permeate into the permeate side and thereby removed.

In terms of the material of the reverse osmosis membrane used in the present invention, examples of the membrane include composite membranes having a cellulose acetate polymer functional layer (hereinafter referred to as cellulose acetate reverse osmosis membranes) and composite membranes having a polyamide functional layer (hereinafter referred to as polyamide reverse osmosis membranes). Examples of the cellulose acetate polymer herein include polymers prepared with organic acid esters of cellulose such as cellulose acetate, cellulose diacetate, cellulose triacetate, cellulose propionate and cellulose butyrate, which may be used solely, as a mixture, or as a mixed ester. Examples of the polyamide include linear polymers and cross-linked polymers constituted by aliphatic and/or aromatic diamine monomers.

Specific examples of the reverse osmosis membrane preferably used in the present invention include polyamide reverse osmosis membranes UTC-70, SU-710, SU-720, SU-720F, SU-710L, SU-720L, SU-720LF, SU-720R, SU-710P, SU-720P, SU-810, SU-820, SU-820L, SU-820FA, SUL-G10, SUL-G20, SUL-G20F, SUL-G10P, SUL-G20P, TM800 series, TM800C series, TM800A series, TM800H series, TM800E series and TM800L series, manufactured by Toray Industries, Inc.; cellulose acetate reverse osmosis membranes SC-L100R, SC-L200R, SC-1100, SC-1200, SC-2100, SC-2200, SC-3100, SC-3200, SC-8100 and SC-8200, manufactured by Toray Industries, Inc.; NTR-759HR, NTR-729HF, NTR-70SWC, ES10-D, ES20-D, ES20-U, ES15-D, ES15-U and LF10-D, manufactured by Nitto Denko Corporation; RO98pHt, RO99, HR98PP and CE4040C-30D, manufactured by Alfa-Laval; A Series, GE Sepa, HL Series, Duraslick Series, MUNI RO Series, MUNI RO LE Series, Duratherm RO HF Series, CK Series, DK Series, Seasoft Series, Duratherm RO HF Series, Duratherm HWS Series, PRO RO Series and PRO RO LE Series, manufactured by GE; BLF series, BLR series and BE series, manufactured by SAEHAN CSM; SelRO Series, manufactured by KOCH; and BW30-4040, TW30-4040, XLE-4040, LP-4040, LE-4040, SW30-4040 and SW30HRLE-4040, manufactured by FilmTec Corporation.

In term of the form of the membrane, flat membranes, spiral-wound membranes, hollow fiber membranes and the like may be used as appropriate.

In terms of the membrane separation performance of the reverse osmosis membrane used in the present invention, the reverse osmosis membrane shows a sodium chloride removal rate of preferably not less than 90%, more preferably not less than 95% when sodium chloride (raw liquid sodium chloride concentration, 3.5%) at a temperature of 25° C. and a pH of 6.5 is used at a filtration pressure of 5.5 MPa. The sodium chloride removal rate can be calculated according to Equation 1.

In terms of the permeation performance of the reverse osmosis membrane, a membrane having a membrane permeation flux ($m^3/(m^2 \cdot day)$) of not less than 0.2 for sodium chloride (3.5%) at a filtration pressure of 5.5 MPa is preferably used since the rate of concentration of the fermentation broth can be increased. The membrane permeation flux herein means a permeation flow rate per unit membrane area per unit pressure, which can be calculated by measuring the amount of the permeate, collection time of the permeate and the membrane area, and using Equation 2.

In the present invention, a reverse osmosis membrane having low permeability to butanol and high permeability to water (water permeability) is preferably used. Examples of the method of evaluation of the permeability of a reverse osmosis membrane to butanol herein include evaluation by calculation of the butanol permeation rate. The butanol permeation rate can be calculated by measuring the concentration of butanol contained in the raw liquid (feed liquid) (raw liquid butanol concentration) and the concentration of butanol contained in the permeate (butanol-containing solution) (permeate butanol concentration) by an analysis represented by high performance liquid chromatography, and using Equation 3.

The filtration through a reverse osmosis membrane may be carried out under pressure, and the filtration pressure is preferably within the range of 0.1 MPa to 8 MPa. In cases where the filtration pressure is less than 0.1 MPa, the membrane permeation rate may decrease, while in cases where the filtration pressure is more than 8 MPa, the membrane may be damaged. In cases where the membrane is used at a filtration pressure within the range of 0.5 MPa to 7 MPa, the membrane permeation flux is high, so that the aqueous butanol solution can be efficiently concentrated and the possibility of damaging the membrane is small, which is more preferred. The membrane is especially preferably used at a filtration pressure within the range of 1 MPa to 6 MPa.

The temperature of the butanol-containing solution during its concentration through the reverse osmosis membrane is not restricted, and preferably within the range of 4 to 60° C., more preferably within the range of 20 to 50° C. In cases where the temperature of the butanol-containing solution is less than 4° C., the operation of two-phase separation into a butanol phase and an aqueous phase may be difficult, while in cases where the temperature of the butanol-containing solution exceeds 60° C., the reverse osmosis membrane may be damaged and hence the operation of concentration may be unsuccessful.

The concentration of butanol in the concentrate obtained in Step B is not restricted, and preferably not less than 8% by weight, more preferably not less than 15% by weight, still more preferably not less than 30% by weight, and especially preferably not less than 40% by weight. In cases where the butanol concentration is not less than 8% by weight, the concentration exceeds the saturation solubility of butanol to water, leading to separation into two phases, that is, into a butanol phase and an aqueous phase. Upon occurrence of the two-phase separation, the aqueous-phase portion is further concentrated by the reverse osmosis membrane, resulting in migration, into the butanol phase, of butanol in an amount by which the amount of butanol exceeds the saturation solubility. That is, since the butanol concentration is constantly kept at the saturation solubility, it is substantially possible to keep increasing the butanol concentration at a constant osmotic pressure difference. Since the butanol-containing solution to be passed through the reverse osmosis membrane has already been filtered through a nanofiltration membrane, the impurity concentration in the solution is extremely low, so that the osmotic pressure is hardly affected by impurities, which allows concentration at low operating pressure. Further, since impurities having surface activity have been removed by filtration, two-phase separation easily occurs.

(Step C)

Butanol can be obtained by recovering the butanol phase from the butanol concentrate obtained in Step B, which has undergone two-phase separation into the butanol phase and the aqueous phase. Since the obtained butanol has been filtered through a nanofiltration membrane in Step A, the concentration of impurities therein is extremely low. Since butanol remains also in the aqueous phase, which was not recovered, in the amount equivalent to the saturation solubility, the aqueous phase may be recycled as the raw liquid to be subjected to filtration through the nanofiltration membrane in Step A and/or as the raw liquid to be subjected to filtration through the reverse osmosis membrane in Step B, to increase the total recovery of butanol.

Further, by purifying the recovered butanol phase by distillation, butanol with higher purity can be obtained. The step of purification of butanol by distillation is carried out preferably under a reduced pressure of not less than 1 Pa and not more than atmospheric pressure (normal pressure, about 101 kPa), more preferably under a reduced pressure of not less than 100 Pa and not more than 80 kPa, still more preferably under a reduced pressure of not less than 100 Pa and not more than 50 kPa. In cases where the distillation is carried out under reduced pressure, the distillation temperature is preferably not less than 20° C. and not more than 200° C., more preferably not less than 40° C. and not more than 150° C.

In the step of purification of butanol by distillation, butanol with high purity can be mainly recovered from the liquid side. However, since the vapor side contains butanol and water as a result of azeotropy, the condensate recovered from the vapor side may be recycled again into the raw liquid to be subjected filtration through the nanofiltration membrane in Step A and/or into the raw liquid to be subjected to filtration through the reverse osmosis membrane in Step B and/or into the extraction vessel, to increase the total recovery of butanol. Further, by distilling butanol recovered from the liquid side again and recovering butanol from the vapor side, the purity of butanol can be further increased.

Figure 1:
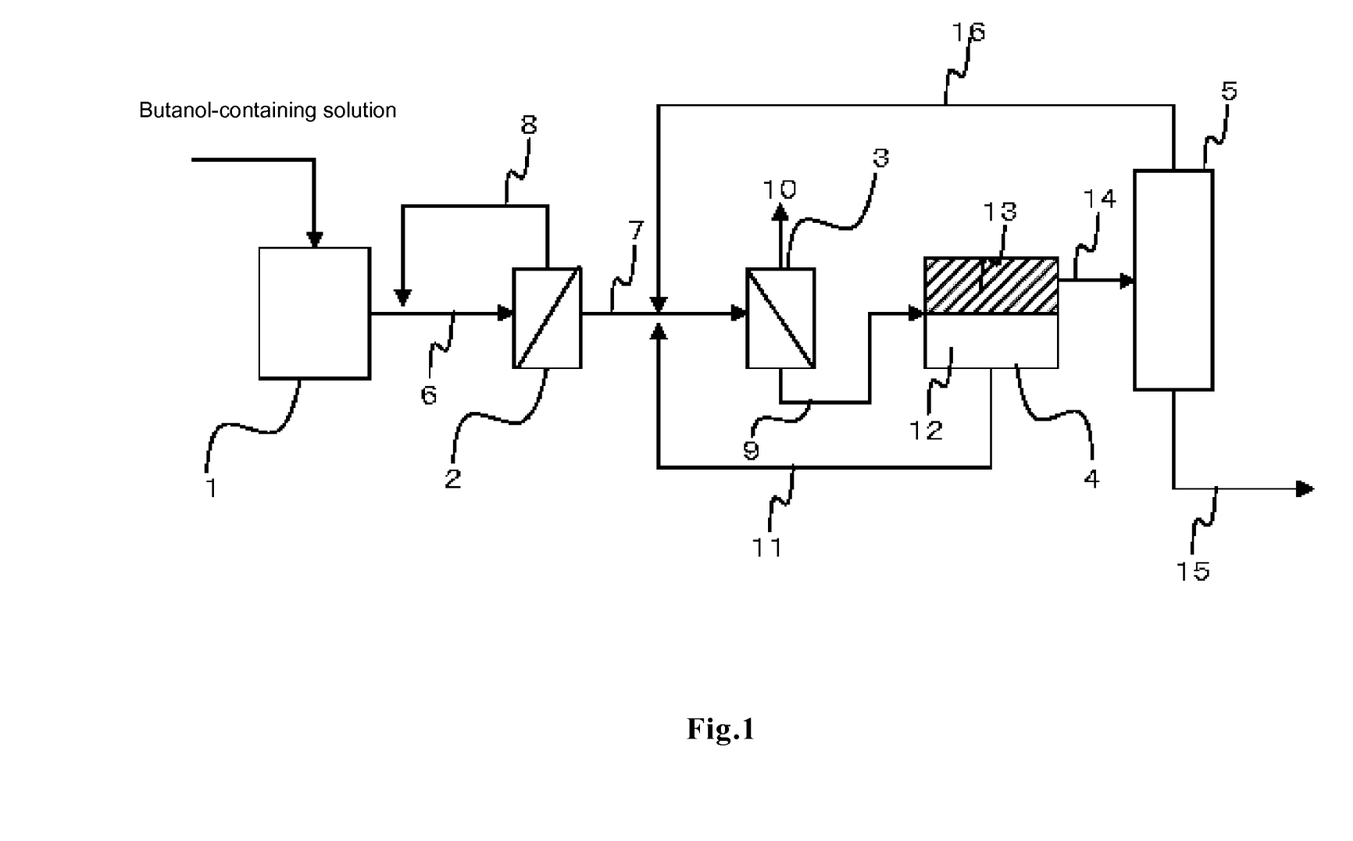
FIG. 1 is a schematic diagram showing a preferred embodiment of the present invention.

An outline of the method of the present invention for producing butanol will now be described referring to a drawing. FIG. 1 shows a preferred embodiment of the present invention, and, in this embodiment, a flow of a butanol-containing solution, 6, is filtered through a nanofiltration membrane to separate the flow into a flow of a butanol-containing permeate, 7, and a flow of a non-permeated liquid containing impurities, 8. The flow of a butanol-containing permeate, 7, is filtered through a reverse osmosis membrane, and the flow of a non-permeated liquid containing a large amount of impurities, 8, is recycled into the flow of an aqueous butanol solution, 6, or into a raw liquid tank 1. The flow 7 subjected to filtration through the reverse osmosis membrane is separated into a flow of a non-permeated liquid wherein butanol is concentrated, 9, and a permeate which does not substantially contain butanol and contains water, 10. The flow of a non-permeated liquid wherein butanol is concentrated, 9, is received by an extraction vessel 4 and undergoes two-phase separation into a butanol phase and an aqueous phase containing butanol in an amount equivalent to the saturation solubility. A flow of the aqueous phase containing butanol in the amount equivalent to the saturation solubility, 11, is recycled into the flow of a butanol-containing permeate, 7, to be subjected to filtration through the reverse osmosis membrane, or into the flow of an aqueous butanol solution, 6, or into the raw liquid tank 1, and a flow of the butanol phase, 14, is sent to a distillation column. The butanol phase sent to the distillation column is recovered from the bottom of the distillation column as a flow of butanol with high purity, 15, and a flow containing butanol and water, 16, is recycled into the flow of a butanol-containing permeate, 7, to be subjected to filtration through a reverse osmosis membrane or into the flow of an aqueous butanol solution, 6, or into the raw liquid tank 1.

EXAMPLES

The present invention will now be described below in more detail by way of Examples, but the present invention is not restricted to the Examples below.

Examples 1 to 4

Separation/Purification of Isobutanol Model Fermentation Broth (Preparation of Isobutanol Model Fermentation Broth)

A solution was prepared such that it contains, in 48 L of pure water, 10% by weight isobutanol (manufactured by Wako Pure Chemical Industries, Ltd.), 10% by weight glucose (manufactured by Wako Pure Chemical Industries, Ltd.), 5% by weight yeast extract (manufactured by Oriental Yeast Co., Ltd.), 5% by weight zinc sulfate (manufactured by Wako Pure Chemical Industries, Ltd.), 5% by weight ammonium sulfate (manufactured by Wako Pure Chemical Industries, Ltd.) and 5% by weight acetic acid (manufactured by Wako Pure Chemical Industries, Ltd.), followed by adjusting the pH to 6, subjecting the resulting solution to autoclaving (at 121° C. for 20 minutes) and diluting the solution 10-fold with pure water to provide a model fermentation broth. Components contained in the model fermentation broth and purified isobutanol were analyzed by the following measurement methods.

Analysis of Isobutanol Concentration by HPLC
Column used: Luna 5u $NH_2$ 100A (manufactured by Phenomenex, Inc.)
Mobile phase: acetonitrile:water=3:1
Detector: RI.

Analysis of Glucose Concentration by HPLC
Column used: Luna 5u $NH_2$ 100A (manufactured by Phenomenex, Inc.)
Mobile phase: acetonitrile:water=3:1
Detector: RI.

Analysis of Inorganic Ion Concentrations by Ion Chromatography

The concentrations of sulfate ions and acetate ions as impurities were measured under the following conditions.
Column (AS22 (manufactured by Dionex Corporation)), eluent (1.8 mM sodium carbonate/1.7 mM sodium hydrogen carbonate), temperature (35° C.).

Measurement of Degree of Coloration of Aqueous Solution

As an index to represent the degree of purification of the isobutanol-containing solution, APHA (Hazen color number) was used. The measurement was carried out with a color meter for petroleum products, OME 2000 (manufactured by Nippon Denshoku Industries Co., Ltd.).

Analysis of Purity by Gas Chromatography (GC)

A gas chromatography: GC-2010 (manufactured by Shimadzu Corporation) was used to perform an analysis under the following conditions, to calculate the CG purity according to (isobutanol peak area)/(total peak area)×100.
Column: TC-1, 0.53 mm I.D.×15 m, df=1.5 μm (GL Science)
Mobile phase: helium gas (7.9 mL/min., 50 to 200° C.: 5° C./min.)
Detection: FID 250° C.

(Filtration Experiment with Nanofiltration Membrane)

Figure 2:
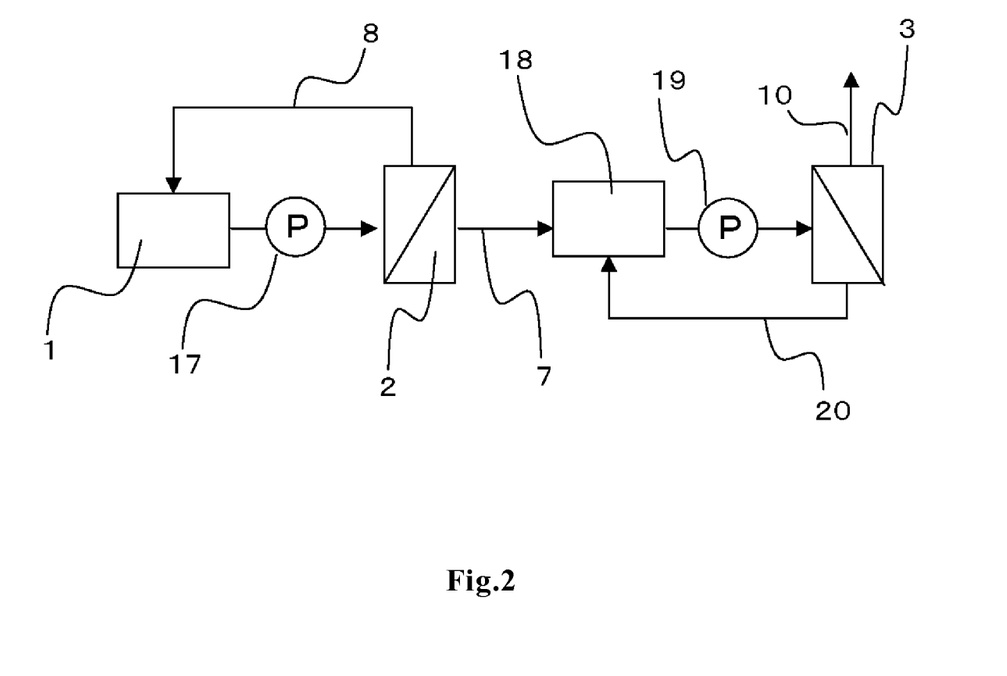
FIG. 2 is a schematic diagram showing a preferred embodiment of the membrane filtration/concentration apparatus used in the present invention.

To the raw liquid tank 1 shown in FIG. 2, 480 L of the isobutanol model fermentation broth obtained as described above was fed. Subsequently, a 4-inch nanofiltration membrane module 2 (SU-610; membrane area, 7 $m^2$; manufactured by Toray Industries, Inc.) was placed in a special container, and a high pressure pump 17 was operated at an operating pressure of 0.5, 1.0, 2.0 or 4.0 MPa (Examples 1 to 4). In this operation, the permeate 7 was recovered, while the non-permeated liquid 8 was returned to the raw liquid tank 1, and, as a result, 470 L of a recovered liquid was obtained. The concentrations of isobutanol, glucose, sulfate ions and acetic acid contained in the model fermentation broth and the recovered liquid; and the degrees of coloration (APHA) of these liquids; were measured. The results are shown in Table 1.

TABLE 1

| | Filtration pressure [MPa] | Membrane permeation flux [m³/m²/day] | Isobutanol concentration | | | Glucose concentration | | |
|---|---|---|---|---|---|---|---|---|
| | | | Model fermentation broth [wt %] | Recovered liquid [wt %] | Permeation rate [%] | Model fermentation broth [wt %] | Recovered liquid [wt %] | Removal rate [%] |
| Example 1 | 0.5 | 0.49 | 1 | 0.63 | 63.3 | 1 | 0.05 | 95.0 |
| Example 2 | 1.0 | 0.97 | 1 | 0.52 | 52.3 | 1 | 0.04 | 96.4 |
| Example 3 | 2.0 | 2.04 | 1 | 0.48 | 48.1 | 1 | 0.04 | 96.4 |
| Example 4 | 4.0 | 4.21 | 1 | 0.45 | 45.0 | 1 | 0.03 | 96.9 |

| | Sulfate ion concentration | | | Acetic acid concentration | | | APHA | |
|---|---|---|---|---|---|---|---|---|
| | Model fermentation broth [wt %] | Recovered liquid [wt %] | Removal rate [%] | Model fermentation broth [wt %] | Recovered liquid [wt %] | Removal rate [%] | Model fermentation broth | Recovered liquid |
| Example 1 | 0.66 | 0.004 | 99.4 | 0.5 | 0.29 | 42.0 | 500 | 1 |
| Example 2 | 0.66 | 0.003 | 99.6 | 0.5 | 0.25 | 50.0 | 500 | 1 |
| Example 3 | 0.66 | 0.002 | 99.7 | 0.5 | 0.22 | 56.0 | 500 | 1 |
| Example 4 | 0.66 | 0.001 | 99.9 | 0.5 | 0.21 | 58.0 | 500 | 1 |

As shown in Table 1, at any of the pressures, an isobutanol-containing solution from which glucose and sulfate ions were efficiently removed by the nanofiltration membrane module was recovered from the permeate side of the nanofiltration membrane. Further, since a clear isobutanol-containing solution (APHA 1) was obtained from the model fermentation broth, which had been brown, it was assumed that other impurities were also removed by the nanofiltration membrane.

(Concentration Experiment with Reverse Osmosis Membrane)

To the raw liquid tank 18, 470 L of the recovered liquid (isobutanol nanofiltration membrane permeate; temperature, 25° C.) obtained in the above Example 3 was fed. Subsequently, a 4-inch reverse osmosis membrane module 3 (TM-810; membrane area, 7 m$^2$; manufactured by Toray Industries, Inc.) was placed in a special container, and the operating pressure of a high pressure pump 19 was adjusted to 5 MPa. The permeate 10 was discharged to the outside of the system, while the non-permeated liquid 20 was returned into the raw liquid tank 18, by which concentration was repeated. The concentrations of isobutanol, glucose and sulfate ions contained in the raw liquid tank 18, and the membrane permeation flux of the permeate 10 were measured. The results are shown in Table 2.

TABLE 2

| Amount of permeate removed [kg] | Concentration in raw liquid [wt %] | | | | Amount of liquid fed [m$^3$/day] | Membrane permeation flux [m$^3$/m$^2$/day] |
| --- | --- | --- | --- | --- | --- | --- |
| | Isobu-tanol | Glu-cose | Sulfate ion | Acetic acid | | |
| 0 | 0.5 | 0.0 | 0.00 | 0.22 | 22.7 | 1.13 |
| 100 | 0.6 | 0.1 | 0.00 | 0.28 | 22.7 | 1.13 |
| 200 | 0.9 | 0.1 | 0.00 | 0.38 | 22.7 | 1.08 |
| 300 | 1.4 | 0.1 | 0.01 | 0.61 | 22.7 | 1.01 |
| 400 | 3.3 | 0.3 | 0.01 | 1.47 | 22.7 | 0.87 |
| 420 | 4.6 | 0.4 | 0.02 | 2.06 | 22.7 | 0.64 |
| 440 | 7.7 | 0.6 | 0.03 | 3.43 | 22.7 | 0.48 |
| 445 | 9.2 | 0.8 | 0.04 | 4.12 | 22.7 | 0.41 |
| 450 | 11.5 | 0.9 | 0.05 | 5.15 | 22.7 | 0.33 |
| 455 | 15.3 | 1.3 | 0.06 | 6.87 | 22.7 | 0.33 |
| 460 | 23.0 | 1.9 | 0.09 | 10.30 | 22.7 | 0.33 |

As shown in Table 2, when isobutanol was concentrated through the reverse osmosis membrane module to a high concentration and the concentration in the raw liquid tank reached the saturation solubility (8% by weight), two-phase separation of the aqueous solution in the raw liquid tank was observed. From the time of two-phase separation, the operation was carried out such that the lower-phase portion (aqueous phase) was substantially returned to the raw liquid tank, and the concentration proceeded without any decrease in the amount of the permeate, with a constant membrane permeation flux. The raw liquid after the concentration was recovered and isobutanol in the upper phase was recovered, and the recovery was found to be 60.1% (Experiment 1). When the same experiment was repeated, the recovery of isobutanol was found to be 71.5% (Experiment 2).

(Distillation of Isobutanol)

The isobutanol phase recovered in Experiment 2 was distilled at 10 kPa at 80° C., or at normal pressure at 95° C., and the vapor side was recovered. The results are shown in Table 3.

TABLE 3

| | Distillation condition | Concentration [wt %] | | | | | Distillation yield [%] | GC purity [%] |
| --- | --- | --- | --- | --- | --- | --- | --- | --- |
| | | Isobutanol | Glucose | Sulfate ion | Acetic acid | APHA | | |
| Before distillation | — | 84.3 | 0.30 | 0.15 | 0.08 | 38 | — | 89.9 |
| After distillation | 10 kPa | 100.0 | 0.00 | 0.00 | 0.00 | 3 | 95 | 99.9 |
| After distillation | Normal pressure | 83.9 | 0.00 | 0.00 | 0.00 | 3 | 98 | 99.9 |

As shown in Table 3, as a result of the distillation, isobutanol with low degree of coloration and at high purity could be obtained. The distillation yields were as high as 95% and 98%, respectively.

Examples 5 to 7

Concentration/Separation of Nanofiltration-Membrane Permeate by Reverse Osmosis Membrane A model fermentation broth was prepared in the same manner as described above such that the initial concentration of isobutanol was 1.5, 2.0 or 3.0% by weight (Examples 5 to 7). This was subjected to be filtered through the nanofiltration membrane at 2.0 MPa in the same manner as in Example 3, and a permeate was obtained. The permeate in an amount of 460 L each was further subjected to removal/concentration using the reverse osmosis membrane module under the same conditions as in Example 3, and the isobutanol phase was recovered from the raw liquid tank after the concentration. The results of evaluation of the recovery of isobutanol are shown in Table 4.

TABLE 4

| | Isobutanol concentration [wt %] | | | Isobutanol | |
| --- | --- | --- | --- | --- | --- |
| | Model fermentation broth | Nano-filtration membrane-permeated liquid | After concentration with reverse osmosis membrane | Amount recovered [kg] | Recovery rate [%] |
| Example 5 | 1.5 | 0.72 | 33.8 | 2.3 | 69.4 |
| Example 6 | 2.0 | 0.96 | 45.1 | 3.7 | 83.8 |
| Example 7 | 3.0 | 1.44 | 67.7 | 6.0 | 90.6 |

As shown in Table 4, it was revealed that, as the isobutanol concentration after the concentration operation increases, the recovery of isobutanol increases. Further, it was suggested that, even if the amount of isobutanol dissolved in the aqueous phase is not taken into account, a higher concentration after the concentration operation results in a higher recovery. It could be confirmed that the operation/concentration can be stably carried out until the isobutanol concentration reaches 67% by weight.

Comparative Example 1

Concentration Experiment, and Purification, by Distillation, of Isobutanol Model Fermentation Broth with Reverse Osmosis Membrane The above-described isobutanol model fermentation broth was prepared in an amount of 470 L, and its concentration/two-phase separation with the reverse osmosis membrane was attempted under the same conditions as in Example 3 without carrying out filtration through the nanofiltration membrane.

(Concentration Experiment with Reverse Osmosis Membrane)

To the raw liquid tank 18 shown in FIG. 2, 470 L (temperature, 25° C.) of an isobutanol model fermentation broth prepared in the same manner as in Examples 1 to 4 was fed, and a 4-inch reverse osmosis membrane module 3 (TM-810; membrane area, 7 m$^2$; manufactured by Toray Industries, Inc.) was placed in a special container, followed by adjusting the pressure of the high pressure pump 19 to 5 MPa. The operation was carried out by discharging the permeate 10 to the outside of the system, while returning the non-permeated liquid 20 to the raw liquid tank 18. The concentrations of isobutanol, glucose and sulfate ions contained in the raw liquid tank 18, and the membrane permeation flux of the permeate 10 were measured. The results are shown in Table 5.

TABLE 5

| Amount of permeate removed [kg] | Concentration in raw liquid [wt %] | | | | Amount of liquid fed [m$^3$/day] | Membrane permeation flux [m$^3$/m$^2$/day] |
| --- | --- | --- | --- | --- | --- | --- |
| | Isobu-tanol | Glu-cose | Sulfate ion | Acetic acid | | |
| 0 | 1.0 | 1.0 | 0.66 | 0.50 | 22.7 | 0.21 |
| 100 | 1.2 | 1.2 | 0.84 | 0.50 | 22.7 | 0.21 |
| 200 | 1.7 | 1.7 | 1.15 | 0.64 | 22.7 | 0.20 |
| 300 | 2.7 | 2.7 | 1.82 | 0.87 | 22.7 | 0.19 |
| 400 | 6.6 | 6.6 | 4.43 | 1.38 | 22.7 | 0.16 |
| 420 | 9.2 | 9.2 | 6.20 | 3.36 | 22.7 | 0.12 |
| 440 | 15.3 | 15.3 | 10.33 | 4.70 | 22.7 | 0.09 |

As shown in Table 5, isobutanol was concentrated by the reverse osmosis membrane module. However, since the isobutanol model fermentation broth comprised a large amount of impurities, the amount of the permeate was low due to the influence of the osmotic pressure. As the concentration continued, the membrane permeation flux further decreased, and the membrane permeation flux became 0 when the amount of permeate exceeded 440 L, so that the experiment was terminated. At this time, 30 L of the solution was remaining in the raw liquid tank and was separated into two phases as in Example 3. However, the interface between the phases was fuzzy and the two-phase separability was low. The upper phase was recovered, and the recovery of isobutanol was found to be 32.6%.

(Distillation of Isobutanol)

The isobutanol phase recovered as described above was subjected to distillation as in Example 3 at 10 kPa at 80° C., or at normal pressure at 95° C., and the vapor side was recovered. The results are shown in Table 6.

TABLE 6

| | Distillation condition | Concentration [wt %] | | | | | Distillation yield [%] | GC purity [%] |
| --- | --- | --- | --- | --- | --- | --- | --- | --- |
| | | Isobutanol | Glucose | Sulfate ion | Acetic acid | APHA | | |
| Before distillation | — | 68.5 | 6.39 | 4.55 | 3.26 | 351 | — | 80.9 |
| After distillation | 10 kPa | 99.0 | 0.00 | 0.00 | 0.01 | 96 | 75 | 94.2 |
| After distillation | Normal pressure | 62.8 | 0.00 | 0.00 | 0.05 | 96 | 83 | 99.5 |

As shown in Table 6, the isobutanol obtained by the distillation showed a high degree of coloration, and the distillation yields were 75% and 83%, respectively.

Examples 8 to 11

Separation/Purification of n-Butanol Model Fermentation Broth (Preparation of n-Butanol Model Fermentation Broth)

A solution was prepared such that it contains, in 48 L of pure water, 10% by weight n-butanol (manufactured by Wako Pure Chemical Industries, Ltd.), 10% by weight glucose (manufactured by Wako Pure Chemical Industries, Ltd.), 5% by weight yeast extract (manufactured by Oriental Yeast Co., Ltd.), 5% by weight zinc sulfate (manufactured by Wako Pure Chemical Industries, Ltd.), 5% by weight ammonium sulfate (manufactured by Wako Pure Chemical Industries, Ltd.) and 5% by weight acetic acid (manufactured by Wako Pure Chemical Industries, Ltd.), followed by adjusting the pH to 6, subjecting the resulting solution to autoclaving (at 121° C. for 20 minutes), and diluting the solution 10-fold with pure water to provide a model fermentation broth. Components contained in the model fermentation broth and purified n-butanol were analyzed by the same measurement methods as those for the cases of isobutanol described in Examples 1 to 7 and Comparative Example 1, (Filtration Experiment with Nanofiltration Membrane)

To the raw liquid tank 1 shown in FIG. 2, 480 L of the n-butanol model fermentation broth obtained as described above was fed. Subsequently, a 4-inch nanofiltration membrane module 2 (SU-610; membrane area, 7 $m^2$; manufactured by Toray Industries, Inc.) was placed in a special container, and a high pressure pump 17 was operated at an operating pressure of 0.5, 1.0, 2.0 or 4.0 MPa, (Examples 5 to 8). In this operation, the permeate 7 was recovered, while the non-permeated liquid 8 was returned to the raw liquid tank 1, and, as a result, 470 L of a recovered liquid was obtained. The concentrations of n-butanol, glucose, sulfate ions and acetic acid contained in the model fermentation broth and the recovered liquid; and the degree of coloration (APHA); were measured. The results are shown in Table 7.

tained in the raw liquid tank 18, and the membrane permeation flux of the permeate 10 were measured. The results are shown in Table 8.

TABLE 8

| Amount of permeate removed [kg] | Concentration in raw liquid [wt %] | | | | Amount of liquid fed [$m^3$/day] | Membrane permeation flux [$m^3/m^2$/day] |
|---|---|---|---|---|---|---|
| | n-Butanol | Glucose | Sulfate ion | Acetic acid | | |
| 0 | 0.7 | 0.0 | 0.00 | 0.08 | 22.7 | 1.10 |
| 100 | 0.9 | 0.1 | 0.00 | 0.10 | 22.7 | 1.10 |
| 200 | 1.2 | 0.1 | 0.00 | 0.14 | 22.7 | 1.05 |
| 300 | 1.9 | 0.1 | 0.01 | 0.22 | 22.7 | 1.01 |
| 400 | 4.7 | 0.3 | 0.01 | 0.54 | 22.7 | 0.88 |
| 420 | 6.6 | 0.5 | 0.02 | 0.70 | 22.7 | 0.62 |
| 440 | 10.9 | 0.6 | 0.03 | 1.22 | 22.7 | 0.36 |
| 445 | 13.2 | 0.8 | 0.04 | 1.50 | 22.7 | 0.36 |
| 450 | 16.5 | 1.0 | 0.05 | 1.85 | 22.7 | 0.36 |

TABLE 7

| | Filtration pressure [MPa] | Membrane permeation flux [$m^3/m^2$/day] | n-Butanol Concentration | | | Glucose concentration | | |
|---|---|---|---|---|---|---|---|---|
| | | | Model fermentation broth [wt %] | Recovered liquid [wt %] | Permeation rate [%] | Model fermentation broth [wt %] | Recovered liquid [wt %] | Removal rate [%] |
| Example 8 | 0.5 | 0.50 | 1 | 0.83 | 83.3 | 1 | 0.05 | 95.0 |
| Example 9 | 1.0 | 0.98 | 1 | 0.77 | 77.4 | 1 | 0.04 | 96.4 |
| Example 10 | 2.0 | 2.00 | 1 | 0.69 | 68.8 | 1 | 0.04 | 96.4 |
| Example 11 | 4.0 | 4.16 | 1 | 0.61 | 61.2 | 1 | 0.03 | 96.9 |

| | Sulfate ion concentration | | | Acetic acid concentration | | | APHA | |
|---|---|---|---|---|---|---|---|---|
| | Model fermentation broth [wt %] | Recovered liquid [wt %] | Removal rate [%] | Model fermentation broth [wt %] | Recovered liquid [wt %] | Removal rate [%] | Model fermentation broth | Recovered liquid |
| Example 8 | 0.66 | 0.004 | 99.4 | 0.5 | 0.12 | 76.0 | 500 | 1 |
| Example 9 | 0.66 | 0.003 | 99.6 | 0.5 | 0.10 | 80.0 | 500 | 1 |
| Example 10 | 0.66 | 0.002 | 99.7 | 0.5 | 0.08 | 84.0 | 500 | 1 |
| Example 11 | 0.66 | 0.001 | 99.9 | 0.5 | 0.04 | 92.0 | 500 | 1 |

As shown in Table 7, at any of the pressures, an n-butanol-containing solution from which glucose and sulfate ions were efficiently removed by the nanofiltration membrane module was recovered from the permeate side of the nanofiltration membrane. Further, since a clear n-butanol-containing solution (APHA 1) was obtained from the model fermentation broth, which had been brown, it was assumed that other impurities were also removed through the nanofiltration membrane.

(Concentration Experiment with Reverse Osmosis Membrane)

To the raw liquid tank 18, 470 L of the recovered liquid (n-butanol nanofiltration membrane permeate; temperature, 25° C.) obtained in the above Example 10 was fed. Subsequently, a 4-inch reverse osmosis membrane module 3 (TM-810; membrane area, 7 $m^2$; manufactured by Toray Industries, Inc.) was placed in a special container, and the operating pressure of a high pressure pump 19 was adjusted to 5 MPa. The permeate 10 was discharged to the outside of the system, while the non-permeated liquid 20 was returned into the raw liquid tank 18, by which concentration was repeated. The concentrations of n-butanol, glucose and sulfate ions con- TABLE 8-continued

| Amount of permeate removed [kg] | Concentration in raw liquid [wt %] | | | | Amount of liquid fed [$m^3$/day] | Membrane permeation flux [$m^3/m^2$/day] |
|---|---|---|---|---|---|---|
| | n-Butanol | Glucose | Sulfate ion | Acetic acid | | |
| 455 | 21.9 | 1.3 | 0.06 | 2.50 | 22.7 | 0.36 |
| 460 | 32.9 | 1.7 | 0.09 | 3.74 | 22.7 | 0.36 |

As shown in Table 8, when n-butanol was concentrated through the reverse osmosis membrane module to a high concentration and the concentration in the raw liquid tank reached the saturation solubility (8% by weight), two-phase separation of the aqueous solution in the raw liquid tank was observed. From the time of two-phase separation, the operation was carried out such that the lower-phase portion (aqueous phase) was substantially returned to the raw liquid tank, and the concentration proceeded without any decrease in the amount of the permeate, with a constant membrane permeation flux. The raw liquid which was concentrated until the amount of the permeated liquid reached 460 L was recovered and n-butanol in the upper phase was recovered, and the recovery of n-butanol was found to be 83.1%.

(Distillation of n-Butanol)

The n-butanol phase recovered as described above was distilled at normal pressure at 95° C. and the vapor side was recovered. The results are shown in Table 9.

TABLE 9

| | Concentration [wt %] | | | | Distillation yield [%] | GC purity [%] |
|---|---|---|---|---|---|---|
| | n-Butanol | Glucose | Sulfate ion | Acetic acid | APHA | | |
| Before distillation | 84.0 | 0.42 | 0.02 | 0.90 | 25 | — | 98.9 |
| After distillation | 83.6 | 0.00 | 0.00 | 0.00 | 3 | 98 | 99.9 |

As shown in Table 9, as a result of the distillation, n-butanol with low degree of coloration and at high purity could be obtained. The distillation yield was as high as 98%.

Examples 12 to 14

Concentration/Separation of Nanofiltration-Membrane Permeate by Reverse Osmosis Membrane A model fermentation broth was prepared similarly to the above-described cases, such that the initial concentration of n-butanol was 1.5, 2.0 or 3.0% by weight (Examples 12 to 14). This was subjected to be filtered through the nanofiltration membrane at 2.0 MPa in the same manner as in Example 3, and a permeate was obtained. The permeate in an amount of 455 L each was further subjected to removal/concentration using the reverse osmosis membrane module under the same conditions as in Example 10, and the n-butanol phase was recovered from the raw liquid tank after the concentration. The results of evaluation of the recovery of n-butanol are shown in Table 10.

TABLE 10

| | n-Butanol Concentration [wt %] | | | n-Butanol | |
|---|---|---|---|---|---|
| | Model fermentation broth | Nanofiltration membrane-permeated liquid | After concentration with reverse osmosis membrane | Amount recovered [kg] | Recovery rate [%] |
| Example 12 | 1.5 | 1.03 | 33.9 | 4.0 | 83.5 |
| Example 13 | 2.0 | 1.38 | 43.2 | 5.9 | 90.5 |
| Example 14 | 3.0 | 2.08 | 64.6 | 9.5 | 97.5 |

As shown in Table 10, it was revealed that, as the n-butanol concentration after the concentration operation increases, the recovery of n-butanol increases. Further, it was suggested that, even if the amount of n-butanol dissolved in the aqueous phase is not taken into account, a higher concentration after the concentration operation results in a higher recovery. It could be confirmed that the operation/concentration can be stably carried out until the n-butanol concentration reaches about 65% by weight.

From the above Examples and Comparative Example, it was revealed that butanol can be recovered at high efficiency and high purity by filtering a butanol-containing solution through a nanofiltration membrane and recovering a butanol-containing solution from the permeate side, followed by passing the obtained butanol-containing solution through a reverse osmosis membrane and thereby concentrating the solution to cause two-phase separation into a butanol phase and an aqueous phase.

INDUSTRIAL APPLICABILITY

Butanol obtained by the present invention is highly pure, and can be used as a raw material of chemicals and pharmaceuticals, and as a solvent and a fuel.

The invention claimed is:

1. A method for producing butanol, said method comprising:
   a) filtering a microbial fermentation solution containing butanol through a nanofiltration membrane;
   b) recovering a filtered solution from the nanofiltration membrane;
   c) passing the filtered solution from step b) through a reverse osmosis membrane and obtaining a butanol concentrated solution;
   d) separating the butanol concentrated solution of step c) and causing a two-phase separation into a butanol phase and an aqueous phase; and
   e) recovering a butanol product from the butanol phase of step d).

2. The method for producing butanol according to claim 1, wherein said butanol is n-butanol or isobutanol.

3. The method for producing butanol according to claim 1, wherein said nanofiltration membrane has a functional layer that comprises a polyamide.

4. The method for producing butanol according to claim 3, wherein said polyamide comprises a cross-linked piperazine as a major component and further comprises a constituting component represented by Chemical Formula 1:

wherein R represents —H or —CH$_3$, and n represents an integer of 0 to 3.

5. The method for producing butanol according to claim 1, wherein, the temperature of said butanol-containing solution during separation into the butanol and aqueous phases of step c) is within the range of 4 to 60° C.

6. The method for producing butanol according to claim 1, wherein separation into the butanol phase and aqueous phase of step d) is carried out such that the butanol concentration in the butanol phase is not less than 8% by weight.

7. The method for producing butanol according to claim 1, wherein said aqueous phase of step d) is recycled into a flow that is passed through said nanofiltration membrane in step a) and/or said reverse osmosis membrane in step c).

8. The method for producing butanol according to claim 1, wherein the butanol product is recovered by distilling the butanol phase to form a butanol-containing liquid and a vapor, and recovering the butanol product from the liquid and vapor in step e).

9. The method for producing butanol according to claim 8, wherein said butanol product recovered from the vapor during the distilling step is recycled into a flow that is passed through said nanofiltration membrane in step a) and/or said reverse osmosis membrane in step c).

10. The method for producing butanol according to claim 8, wherein said butanol product recovered from the butanol-containing liquid during distillation is further subjected to purification by another distillation, followed by recovering butanol product from the butanol-containing vapor.

11. The method for producing butanol according to claim 1, wherein the temperature of the filtered solution during step c) is within the range of 4 to 60° C.

12. A method for producing butanol, the method comprising:
   a) filtering a microbial fermentation solution containing impurities and butanol through a nanofiltration membrane carried out under pressure of 0.1 MPa to 8 MPa;
   b) recovering a filtered solution from the nanofiltration membrane;
   c) passing the filtered solution from step b) through a reverse osmosis membrane at a filtration pressure of 0.1 MPa to 8 MPa and obtaining a butanol concentrated solution, wherein the temperature of the filtered solution is 4 to 60 degrees Celsius;
   d) separating the butanol concentrated solution of step c) and causing a two-phase separation into a butanol phase and an aqueous phase;
   e) distilling the butanol phase obtained in step d) under a pressure not less than 1 Pa and not more than atmospheric pressure, wherein the distilling is conducted at a temperature not less than 20 degrees Celsius and not more than 200 degrees Celsius, the distilling having a vapor side and a butanol enriched liquid side; and
   f) recovering the butanol enriched liquid side from step d).

13. The method for producing butanol according to claim 12, wherein said butanol is n-butanol or isobutanol.

14. The method for producing butanol according to claim 12, wherein said nanofiltration membrane has a functional layer that comprises a polyamide.

15. The method for producing butanol according to claim 14, wherein said polyamide comprises a cross-linked piperazine as a major component and further comprises a constituting component represented by Chemical Formula 1:

wherein R represents —H or —CH$_3$, and n represents an integer of 0 to 3.

16. A method for producing butanol, the method comprising:
   a) filtering a microbial fermentation solution containing impurities and butanol through a nanofiltration membrane carried out under pressure of 0.1 MPa to 8 MPa, wherein the nanofiltration membrane has a functional layer that comprises a cross-linked piperazine as a major component and further comprises a constituting component represented by Chemical Formula 1:

wherein R represents —H or —CH$_3$, and n represents an integer of 0 to 3;
   b) recovering a filtered solution from the nanofiltration membrane;
   c) passing the filtered solution from step b) through a reverse osmosis membrane at a filtration pressure of 0.1 MPa to 8 MPa and obtaining a butanol concentrated solution, wherein the temperature of the filtered solution is 4 to 60 degrees Celsius;
   d) separating the butanol concentrated solution of step c) and causing a two-phase separation into a butanol phase and an aqueous phase, wherein the butanol phase is not less than 8% by weight;
   e) distilling the butanol phase obtained in step d) under a pressure not less than 1 Pa and not more than atmospheric pressure, wherein the distilling is conducted at a temperature not less than 20 degrees Celsius and not more than 200 degrees Celsius, the distilling having a vapor side and a butanol enriched liquid side; and
   f) recovering the butanol enriched liquid side from step e).

* * * * *